(12) United States Patent
Canady

(10) Patent No.: US 7,122,035 B2
(45) Date of Patent: Oct. 17, 2006

(54) BIPOLAR SURGICAL FORCEPS WITH ARGON PLASMA COAGULATION CAPABILITY

(76) Inventor: Jerome Canady, 1119 Jefferson St., McKeesport, PA (US) 15132

(*) Notice: Subject to any disclaimer, the term of this patent is extended or adjusted under 35 U.S.C. 154(b) by 0 days.

(21) Appl. No.: 10/987,692

(22) Filed: Nov. 12, 2004

(65) Prior Publication Data
US 2005/0107786 A1 May 19, 2005

Related U.S. Application Data

(60) Provisional application No. 60/519,767, filed on Nov. 13, 2003.

(51) Int. Cl.
*A61B 18/18* (2006.01)

(52) U.S. Cl. .......................... 606/52; 606/49

(58) Field of Classification Search .................. 606/41, 606/48–52
See application file for complete search history.

(56) References Cited

U.S. PATENT DOCUMENTS

| | | | |
|---|---|---|---|
| 4,040,426 A | 8/1977 | Morrison | |
| 4,781,175 A | 11/1988 | McGreevy | |
| 5,108,392 A * | 4/1992 | Spingler | 606/51 |
| 5,122,138 A | 6/1992 | Manwaring | |
| 5,207,675 A * | 5/1993 | Canady | 606/40 |
| 5,217,460 A * | 6/1993 | Knoepfler | 606/52 |
| 5,330,469 A | 7/1994 | Fleenor | |
| 5,464,405 A * | 11/1995 | Fujitsu et al. | 606/51 |
| 5,542,945 A | 8/1996 | Fritzsch | |
| 5,556,397 A | 9/1996 | Long et al. | |
| 5,603,712 A * | 2/1997 | Koranda et al. | 606/51 |
| 5,658,281 A | 8/1997 | Heard | |
| 5,720,745 A | 2/1998 | Farin et al. | |
| 5,746,739 A * | 5/1998 | Sutter | 606/51 |
| 6,149,620 A | 11/2000 | Baker et al. | |
| 6,197,026 B1 | 3/2001 | Farin et al. | |
| 6,231,574 B1 | 5/2001 | Posthuma | |
| 6,283,963 B1 | 9/2001 | Regula | |
| 6,293,946 B1 * | 9/2001 | Thorne | 606/48 |
| 6,458,124 B1 | 10/2002 | Garito | |
| 6,458,125 B1 | 10/2002 | Cosmescu | |
| 6,464,701 B1 | 10/2002 | Hooven et al. | |
| 6,558,379 B1 | 5/2003 | Batchelor et al. | |
| 6,585,735 B1 | 7/2003 | Frazier et al. | |
| 2002/0095152 A1 | 7/2002 | Ciarrocca | |
| 2005/0080413 A1 * | 4/2005 | Canady | 606/49 |

* cited by examiner

*Primary Examiner*—Michael Peffley
(74) *Attorney, Agent, or Firm*—24IP Law Group USA; Timothy R. DeWitt

(57) ABSTRACT

Bipolar surgical forceps having argon plasma coagulation capability are shown. The surgical forceps include in their body a channel for receiving a flexible tube having a wire within it. The flexible tubing and wire within it are connected to a generator that provides electrical energy to the wire and argon or other inert gas to the tube. The flexible tubing travels a portion of the length of the forceps and ends with a coaxial connector in the proximity of the points of the scissors. An argon plasma coagulation sleeve is placed on the point of one or both limbs of the forceps and is connected to the flexible tubing and wire through the coaxial connector.

17 Claims, 5 Drawing Sheets

BIPOLAR SURGICAL FORCEPS WITH ARGON PLASMA COAGULATION CAPABILITY

CROSS-REFERENCE TO RELATED APPLICATIONS

This application claims the benefit of the filing date of U.S. Provisional Application Ser. No. 60/519,767 entitled "Surgical Forceps with Argon Plasma Coagulation Capability," and filed on Nov. 13, 2003 by inventor Jerome Canady.

Related Application: "Surgical Scissors with Argon Plasma Coagulation Capability," U.S. application Ser. No. 10/959,542, filed Oct. 6, 2004, Inventor: Jerome Canady.

The above cross-referenced related applications are hereby incorporated by reference herein in their entirety.

STATEMENT REGARDING FEDERALLY SPONSORED RESEARCH OR DEVELOPMENT

Not applicable.

BACKGROUND OF THE INVENTION

1. Field of the Invention

The present invention relates to bipolar surgical forceps that have argon plasma coagulation capability.

2. Brief Description of the Related Art

Controlling or arresting blood loss is of high priority during surgery so as to avoid or minimize the necessity of introducing foreign blood or blood products into a patient. This has increased in importance due to concern over contamination of the blood supply by viral agents which cause, for example, acquired immune deficiency syndrome (AIDS), hepatitis, and the like.

Standard means for controlling traumatic and surgical blood loss are electrosurgical generators and lasers, which respectively direct high-frequency electrical currents or light energy to localize heat in bleeding vessels so as to coagulate the overlying blood and vessel walls.

Argon beam coagulators additionally have been demonstrated to be effective tissue coagulators. Examples of argon beam coagulators for use in open surgery can be found in U.S. Pat. No. 4,040,426 to Morrison and U.S. Pat. No. 4,781,175 to McGreevy. Argon beam coagulators for use rigid and flexible endoscopy also are known. An example of a device for flexible endoscopy may be seen in U.S. Pat. No. 5,207,675 to the present inventor. In some embodiments in that patent, the inventor disclosed dual modality devices that could be used either for argon plasma coagulation or for traditional electrocautery in an endoscopic environment. The inventor also disclosed an embodiment having the dual modality of argon plasma coagulation and endoscopic biopsy forceps. In that embodiment, argon plasma coagulation could be used by a surgeon while the biopsy forceps were withdrawn inside the flexible endoscopic tube. The biopsy forceps could then be extended and used, but argon plasma coagulation was not performed with the biopsy forceps extended from the end of the tube.

Surgical forceps have been known for many years. More recently, surgical forceps have been provided with electrosurgical capability such that the blades of the scissors may be used both to cut and to cauterize tissue. Electrosurgical forceps having both poles of electrosurgical (RF) energy exposed on the surface of the surgical blades have been referred to as "bipolar" electrosurgical forceps.

An example of bipolar electrosurgical forceps for use in open surgery can be found in U.S. Pat. No. 6,231,574, which is hereby incorporated by reference in its entirety. An open surgery embodiment of U.S. Pat. No. 6,231,574 is shown in FIG. 1. The bipolar forceps shown in FIG. 1 comprise two limbs 10, 11 formed by lengths, 12, 13 of square-section stainless steel wire extending from exposed pointed tips 14, 15 through electrically-insulating grip portions 16, 17 to exposed terminal portions 18, 19 separated by an intervening portion of the electrically insulating material of a plug 21 with the oppositely-facing sides 22, 23 of the terminal portions 18, 19 of the wires slightly raised from the respective upper and lower faces 24, 25 of the uprights 26. These upper and lower faces of the uprights of the H have shallow indentations 27 for snap engagement in a 'Block' fitting (not shown) attached to a cable for connecting to a power supply.

The oppositely-facing sides 28, 29 of the grip portions 16, 17 are provided with series of molded cross-grooves 30 with slightly raised edges 31 to afford a good grip; and the mutually-facing sides 32, 33 of the grip portions are provided with two laterally spaced projections 34 on one side and one intervening projection 35 on the other side to ensure correct alignment of the pointed tips 14, 15 when the forceps are squeezed together.

The terminal portions 18, 19 of the wires 12, 13 are initially of a length slightly in excess of the length of the plug 21, so that during manufacture those excess lengths 18X, 19X and the pointed tip portions 14, 15 can be located in recesses 36, 37 in the respective ends of mould parts 38 (only one of which is shown in FIG. 4) into which the electrically-insulating material is injected, and the excess lengths are cropped off after removing the co-molded forceps from the mould.

This device further comprised shoulder portions 39, 40 for the plug 21 in which shoulder portions the wires 12, 13 are each bent through opposite angles of 90 .degree to bring their terminal portions 18, 19 into close parallel disposition in the plug. Additionally, a web 46 was formed between the grip portions.

A second example of bipolar surgical scissors can be found in U.S. Pat. No. 5,746,739, which is hereby incorporated by reference.

Laparoscopic embodiments of bipolar surgical forceps also are known. An example of such an embodiment can be seen in U.S. Pat. No. 6,585,735, which is hereby incorporated by reference.

The present invention provides dual or trimode capabilities for bipolar surgical forceps such that the dual mode surgical instrument can be used simply to cut tissue, simply to coagulate tissue via argon plasma coagulation, or can be used to simultaneously cut tissue and to coagulate tissue via argon plasma coagulation. A trimodal embodiment provides the user with the flexibility to cut tissue and coagulate tissue either via argon plasma coagulation or via traditional electrocautery.

SUMMARY OF THE INVENTION

Bipolar forceps having argon plasma coagulation capability are shown. In a preferred embodiment a pair of bipolar surgical forceps comprises two limbs; and a channel within at least one of the limbs for receiving a tube, wherein said channel has a port at each end. The pair of bipolar surgical forceps may further comprise a tube extending through the channel; a wire within the tube, the wire having a distal end; and wherein the distal end of said wire is within approximately 4 mm of one of the ports. In the pair of bipolar surgical forceps each of the two limbs may comprise an attachment for a pair of bipolar surgical forceps comprising a body having two sides; a channel having two ports within at least one of the sides of said body; and means for securing the attachment to a limb of a pair of surgical forceps.

In another embodiment of the invention, the bipolar surgical forceps of the present invention comprises two elongated limbs each having a first end and a second end, the limbs being connected to each other near the first ends, a channel within at least one of the limbs, the channel having a port near the second end of the at least one of the limbs, a wire within the channel, the wire having first and second ends, the second end of the wire being near the port in the channel, means for connecting the first end of the wire to a source of electrical energy; and means for connecting the first end of the port to a source of inert gas.

In another embodiment, the invention comprises an attachment for pair of surgical forceps. The attachment comprises a body member, such as a sleeve, having a channel within one side. The body member is placed over one of the limbs of a pair of surgical forceps and secured to the limb by friction or other means. An argon plasma coagulation catheter comprising a tube having a wire within it is placed into the channel such that a distal end of the catheter is within a few millimeters of the tip of the limb.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention.

Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE DRAWINGS

For a more complete understanding of the present invention and the advantages thereof, reference is now made to the following description and the accompanying drawings, in which.

DETAILED DESCRIPTION OF THE PREFERRED EMBODIMENTS

Figure 1:
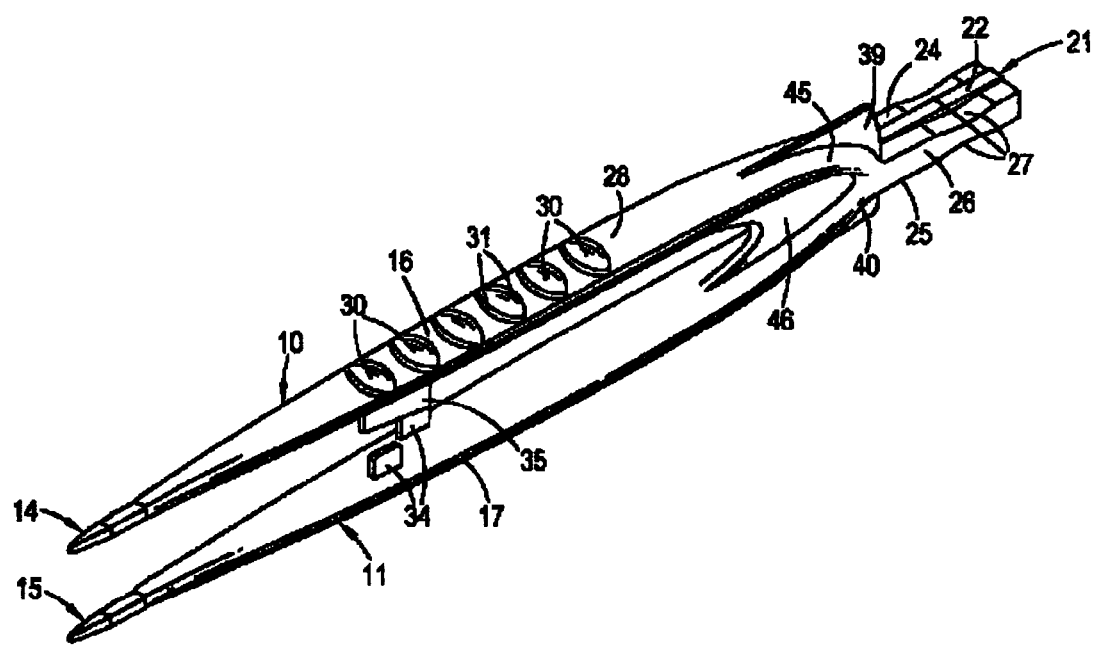
FIG. 1 illustrates a prior art bipolar surgical forceps.
Figure 2:
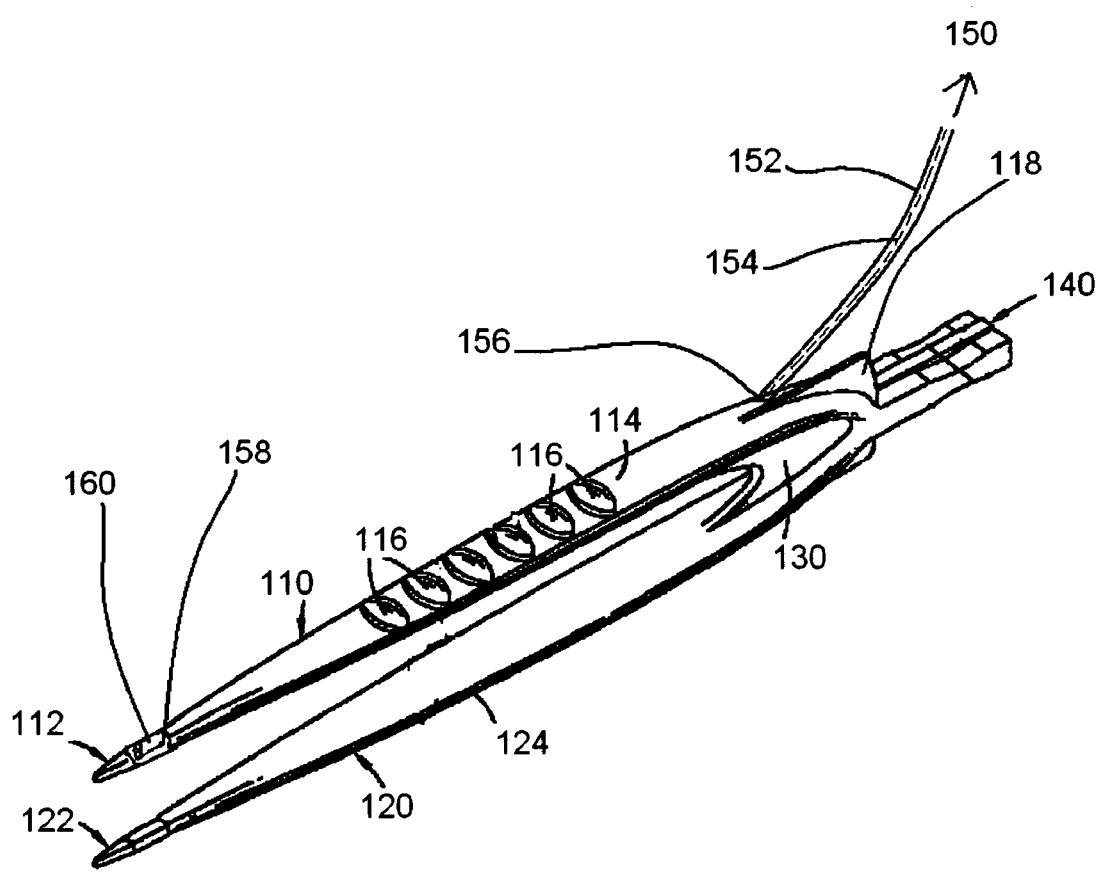
FIG. 2 illustrates a preferred embodiment of bipolar surgical forceps of the present invention.

Referring to FIG. 2, a preferred embodiment of the surgical forceps 100 with argon plasma coagulation capability is shown. The surgical forceps have two limbs 110, 120, each having a pointed tip 112, 122. Each of the two limbs 110, 120 of the bipolar forceps have a conducting element such as a stainless steel or other conducting wire (not shown) extending from the tip 112, 122 to a plug 140 or other connector that connects to an electrosurgical generator (not shown). Such generators are well known in the art.

The wire within each limb 110, 120 is surrounded by an insulating material 114 having grip portions 116 formed therein. A shoulder 118 is formed on each limb 110, 120 and a web 130 is formed between the two limbs 110, 120. A cavity or channel 156 is formed in the insulating layer 114 or between the insulating layer 114 and the stainless steel wire in a limb 110. The channel 156 has an opening near a proximal end portion of the limb 110, on the shoulder 118, or in combination with the plug 140. In FIG. 2, the channel 156 has an opening near the shoulder 128 of limb 110. The channel has a second opening 158 near the tip 112 of limb 110, preferably within about 1 millimeter from the tip 112. The channel 156 is large enough to accommodate an argon plasma coagulation catheter, and preferably is approximately 5 millimeters in diameter, but could be larger or smaller. A channel 156 likewise could be formed in limb 120.

The channel 156 receives a flexible APC catheter comprising a tube 152 and a wire 154 within the tube. The flexible APC catheter has at its distal end a plug or connector for connecting the catheter to an electrosurgical generator and a source of inert gas such as argon 150.

Figure 3:
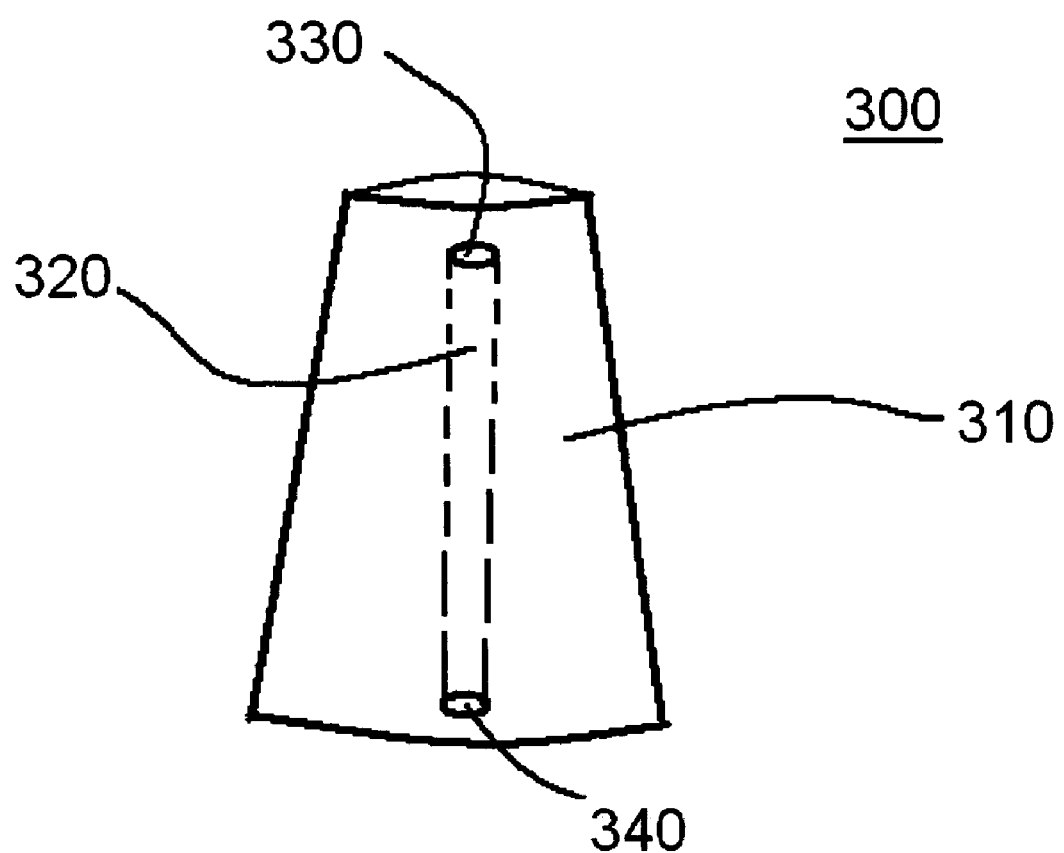
FIG. 3 illustrates another preferred embodiment of an argon plasma coagulation sleeve for use with bipolar forceps in accordance with the present invention.
Figure 4:
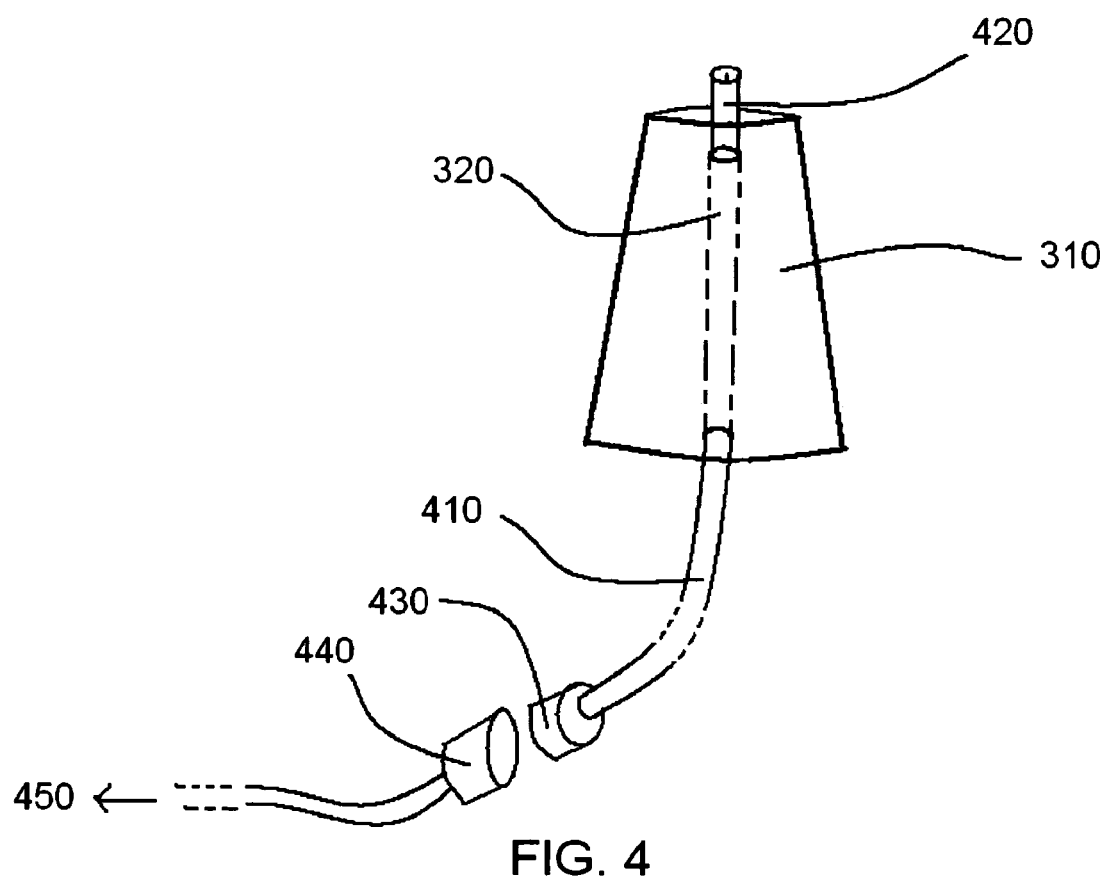
FIG. 4 illustrates an argon plasma coagulation sleeve in accordance with the present invention together with an argon plasma coagulation catheter.
Figure 5:
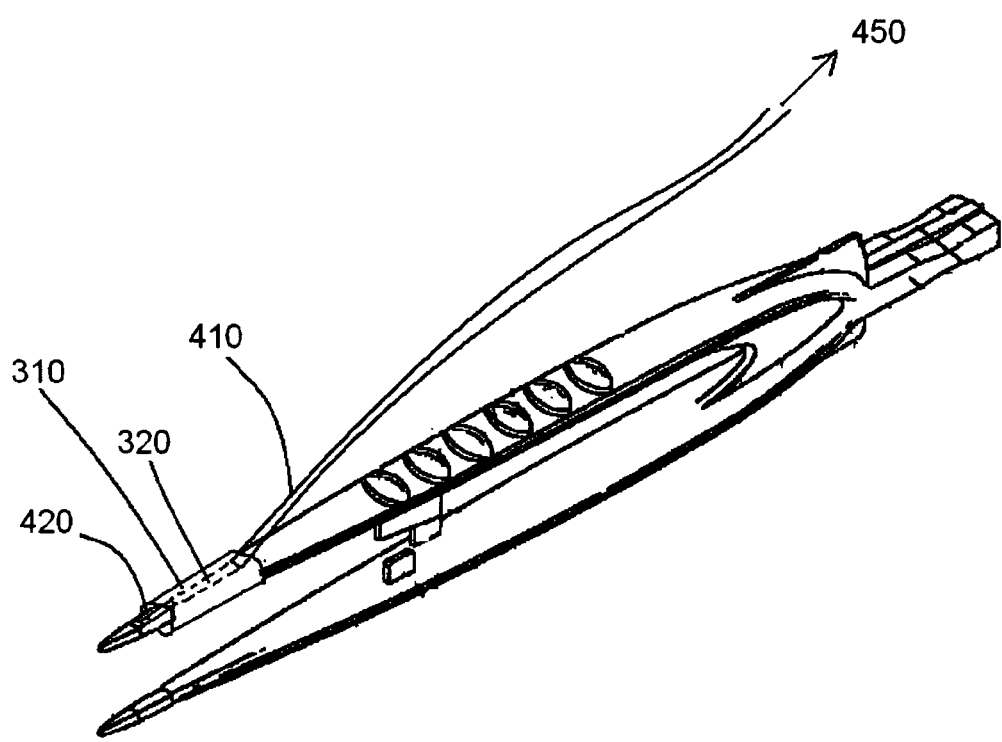
FIG. 5 illustrates an argon plasma coagulation sleeve in accordance with the present invention together with bipolar surgical forceps.

An alternative embodiment is shown in FIGS. 3–5. This particular alternative embodiment a flexible plastic sleeve 300 as shown in FIG. 3. The sleeve 300 has a flexible plastic body having a channel 320 within one side for receiving an argon plasma coagulation catheter. The channel has opening 330 and 340 near the respective ends of the sleeve.

As shown in FIG. 4, a flexible APC catheter 410 is inserted into the channel 320 such that the distal end 420 of the catheter 410. The proximal end of the catheter includes a connector (or plug) 430 for connecting to a source of argon gas 450 and an electrosurgical generator (not shown). One may use an adapter 440 or plug the catheter directly into the APC generator.

In FIG. 5, the sleeve 400 has been inserted onto one limb of a pair of bipolar forceps. The sleeve is positioned such that the APC catheter may extend from the opening in the channel 320 to within about 1 millimeter of the tissue to be treated. Various means may or may not be used to secure the tube 410 of the APC catheter to the forceps above. Means for securing the tube could include a clip, snap, band, glue, or other known securing mechanisms.

In FIG. 5, the APC catheter is shown on the outside of the forceps, but it also could be placed on the inside surface of the forceps. Also, rather than the APC catheter being inserted into a channel in the sleeve, the sleeve could be formed integral with the catheter tube. In yet other embodiments, a clip structure having a channel could be used rather than the sleeve structure shown in FIGS. 3–5. Additionally, the bipolar forceps could be configured to include ridge, depressions, or other structures for retaining an APC sleeve or clip in place on the forceps. These other embodiments will be apparent to those of skill in the art from this disclosure.

During surgery, a surgeon can use the surgical forceps of the present invention in at least for coagulating tissue with argon plasma coagulation, for cauterizing tissue through traditional bipolar cauterization. The surgeon also may use a combination of those.

The sleeves can be placed onto or mounted to the forceps in a variety of different ways and can be formed from a variety of different materials. The sleeves could be composed of a flexible material similar to the material used for the APC tubing, in which case they may be affixed to the forceps via an adhesive or a retaining clip or other securing mechanism as discussed previously. The sleeves alternatively could me made form a hard plastic material such that then could be slid onto or clipped onto the sides of the scissors. The sleeve and clip embodiments allow for inexpensive manufacturing of disposable components.

The present invention likewise may be adapted easily for laparoscopic embodiments. In such a laparoscopic embodiment, a APC tube with a wire within it may extend inside the stem or inside a channel in the stem of a pair of laparoscopic forceps. The APC tube may have a bipolar connector at its distal end. In an alternative embodiment, the APC tube may extend down the outside of the stem and may be affixed to the stem in a variety of different ways such as by glue, an adhesive, or by one or more clips, snaps, or bands.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A pair of surgical forceps comprising:
   two limbs each having a distal end and a proximal end, said distal ends of said two limbs opposing one another and being biased away from one another;
   a channel within one of said limbs for receiving a tube, wherein said channel has a port at each end; and
   a connector for connecting one of said ports of said channel to a source of an inert gas:
   a tube extending through said channel;
   a wire within said tube, said wire having a distal end; and
   wherein said distal end of said wire is within approximately 4 mm of one of said ports
   and said connector connects an end of said tube to said source of an inert gas.

2. A pair of surgical forceps comprising:
   two elongated limbs each having a first end and a second end, said limbs being connected to each other near said first ends;
   a channel within at least one of said limbs, said channel having a port near said second end of said at least one of said limbs;
   a wire within said channel; said wire having first and second ends, said second end being near said port in said channel; and
   means for connecting said first end of said wire to a source of electrical energy and said port to a source of inert gas.

3. A pair of bipolar surgical forceps comprising:
   a first limb comprising a first arm portion, a first tip at a distal end of said first arm portion, a first conducting element extending from said first tip along at least a portion of said first arm to a first connector, a first insulator covering at least a portion of said first conducting element extending along said first arm, and a channel having at its distal end a port near said first tip;
   a second limb comprising a second arm, a second tip at a distal end or said second arm, a second conducting element extending from said second tip along at least a portion of said second arm to a second connector, and a second insulator covering at least a portion of said second conducting means; and
   a connector for connecting a proximal end of said channel to a source of an ionizable inert gas;
   wherein, during surgery, said bipolar surgical forceps may be used to perform argon plasma coagulation.

4. A pair of bipolar surgical forceps according to claim 3 wherein said first tip is pointed.

5. A pair of bipolar surgical forceps according to claim 3 wherein said channel surrounds at least a portion of said first conducting element.

6. A pair of bipolar surgical forceps according to claim 3 wherein said channel is formed within said first insulator.

7. A pair of bipolar surgical forceps according to claim 3 wherein said channel is formed within said first arm.

8. A pair of bipolar surgical forceps according to claim 3 wherein said channel comprises a tube connected to said first arm.

9. A pair of bipolar surgical forceps according to claim 8 wherein at least a portion of said first conducting element is within said tube.

10. A pair of bipolar surgical forceps according to claim 3 wherein a grip is formed on said first insulator.

11. A pair of bipolar surgical forceps according to claim 3 further comprising a wire within said channel.

12. A pair of bipolar surgical forceps according to claim 3 further comprising a tungsten coating on said first tip.

13. A pair of bipolar surgical forceps according to claim 3 wherein said first arm comprises a forward portion adjacent said first tip and a shoulder portion spaced apart from said first tip.

14. A pair of bipolar surgical forceps according to claim 13 wherein said channel has a second port located near said shoulder.

15. A pair of bipolar surgical forceps according to claim 3 wherein said inert gas comprises argon.

16. A pair of bipolar surgical forceps according to claim 3 further comprising:
   a tube within said channel and having a distal end near said port in said channel wherein said connector connects said tube to said source of an ionizable inert gas;
   a wire within said tube, said wire having a distal end near said distal end of said tube; and
   a connector for connecting said wire to a source of RF energy.

17. A pair of bipolar surgical forceps according to claim 3 further comprising:
   a shoulder formed on each of said first and second limbs; and
   a web formed between the first and second limbs.

* * * * *